United States Patent [19]
Goi et al.

[11] 4,158,741
[45] Jun. 19, 1979

[54] PROCESS FOR PREPARING SORBIC ACID

[75] Inventors: Mitsuhiro Goi; Masahiko Miyashita, both of Hirakata; Tokio Hashimoto, Ibaraki, all of Japan

[73] Assignee: Nippon Gohsei Kagaku Kogyo Kabushiki Kaisha, Osaka, Japan

[21] Appl. No.: 737,014

[22] Filed: Oct. 29, 1976

[30] Foreign Application Priority Data

Oct. 30, 1975 [JP] Japan .................................. 50/131282
Dec. 25, 1975 [JP] Japan .................................. 50/155948
Dec. 25, 1975 [JP] Japan .................................. 50/155949
Dec. 27, 1975 [JP] Japan .................................. 50/157319

[51] Int. Cl.$^2$ ........................ C07C 51/00; C07C 57/10
[52] U.S. Cl. .................................... 562/599; 562/600; 562/601

[58] Field of Search ...................... 260/526 N, 535 R; 562/599, 601, 579

[56] References Cited

U.S. PATENT DOCUMENTS

| 2,450,117 | 9/1948 | Caldwell .......................... 260/526 N |
| 4,022,822 | 5/1977 | Tsujiino et al. .................. 260/526 N |

*Primary Examiner*—Vivian Garner
*Attorney, Agent, or Firm*—Armstrong, Nikaido, Marmelstein & Kubovcik

[57] ABSTRACT

Process for preparing sorbic acid which comprises contacting γ-vinyl-γ-butyrolactone with at least one catalyst selected from the group consisting of (A) solid acids, (B) transition metal oxides, (C) metals of Group VIII of the Periodic Table and (D) halides of metals of Groups I-B, II-B, III-B, IV-B, V-B, VI-B and VIII of the Periodic Table.

13 Claims, No Drawings

PROCESS FOR PREPARING SORBIC ACID

BACKGROUND OF THE INVENTION

The present invention relates to a process for preparing sorbic acid, and more particularly to the preparation of sorbic acid from γ-vinyl-γ-butyrolactone with novel catalysts.

Sorbic acid is industrially manufactured by reacting crotonaldehyde with ketene to give a polyester which is formed through an intermediately produced β-lactone and converting the polyester to sorbic acid by heating or by means of acid, base or ion-exchange resin. However, such a process is not necessarily advantageous in point of its procedures or economy because the handling of polyester and the recovery or purification of sorbic acid are troublesome and also because it requires complicated process control.

Two of the present inventors, Masahiko Miyashita and Tokio Hashimoto developed the novel process for preparing sorbic acid by contacting γ-vinyl-γ-butyrolactone with an acid selected from the group consisting of mineral acids, aromatic sulfonic acids, aliphatic sulfonic acids and halogenated carboxylic acids or an acidic cation-exchange resin at an elevated temperature (as shown in U.S. patent application Ser. No. 570,515 filed on Apr. 22, 1975, now U.S. Pat. No. 4,022,822). However, in case of using a cation-exchange resin as a catalyst for cleaving the γ-lactone, a relatively large amount of tarry materials adheres to the catalyst during the use for a long period of time, and it is impossible to use for a long period of time or to reuse such a catalyst because the yield of sorbic acid lowers. Therefore, it is necessary to revive the activity thereof, but very large quantities of a solvent is required for reactivating the catalyst so as to possess a sufficient activity. Also, some of the proposed acid catalysts, for instance, mineral acids, are liquid and, therefore, they cannot be used in the reaction in the vapor phase as they are. Further, the use of a liquid acid such as a mineral acid as a catalyst requires much labor, for instance, the crystals of sorbic acid recovered from the reaction mixture must be sufficiently washed to remove the acid since the acid adheres to the surfaces of the produced crystals of sorbic acid and runs the risk of lowering the qualities of sorbic acid, such as coloring and stability.

OBJECTS OF THE INVENTION

It is an object of the present invention to provide a process for preparing sorbic acid from γ-vinyl-γ-butyrolactone with novel catalysts.

A further object of the invention is to provide a process for economically preparing sorbic acid with simple procedures in high yield.

A still further object of the invention is to provide a catalyst which can be used in the preparation of sorbic acid from γ-vinyl-γ-butyrolactone in both the vapor and liquid phases.

Another object of the invention is to provide a catalyst which is easy to revive the activity lowered due to the adhesion of tarry materials and can be reused.

These and other objects of the invention will become apparent from the description hereinafter.

DETAILED DESCRIPTION

It has now been found that the above-mentioned objects can be accomplished by using at least one catalyst selected from the group consisting of (A) solid acids, (B) transition metal oxides, (C) metals of Group VIII of the Periodic Table and (D) halides of metals of Groups I-B, II-B, III-B, IV-B, V-B, VI-B and VIII of the Periodic Table in the reaction of cleaving γ-vinyl-γ-butyrolactone to sorbic acid. These catalysts are all novel catalysts for preparing sorbic acid from γ-vinyl-γ-butyrolactone.

As the solid acid, clay minerals, salts and double salts of phosphoric acid such as orthophosphoric acid and pyrophosphoric acid, sulfates, boric acid, tungstic acid, phosphotungstic acid, silicotungstic acid, molybdic acid, phosphomolybdic acid, silicomolybdic acid, acetates and propionates are employed in the present invention.

Examples of the clay mineral are alumina, silica, zeolite, synthetic zeolite, bentonite, bauxite, activated clay, diatomaceous earth, silica-alumina, silica-magnesia and alumina-boric anhydride.

Examples of the phosphate are potassium dihydrogenphosphate, dipotassium hydrogenphosphate, sodium dihydrogenphosphate, disodium hydrogenphosphate, barium hydrogenphosphate, calcium hydrogenphosphate, copper phosphate, magnesium phosphate, zinc phosphate, aluminum phosphate, titanium phosphate, zirconium phosphate, chromium phosphate, iron phosphate, cobalt phosphate, nickel phosphate, ruthenium phosphate, rhodium phosphate, palladium phosphate, iridium phosphate and platinum phosphate. Examples of the double salt are double salts of phosphoric acid with metals such as copper, silicon, aluminum, cobalt, iron and boron, for instance, cobalt aluminum phosphate, silicon iron phosphate, cobalt calcium phosphate and copper aluminum phosphate.

Examples of the sulfate are ammonium sulfate, sodium sulfate, sodium hydrogensulfate, potassium sulfate, potassium hydrogensulfate, beryllium sulfate, magnesium sulfate, calcium sulfate, strontium sulfate, barium sulfate, zinc sulfate, cadmium sulfate, aluminum sulfate, cerium sulfate, titanium sulfate, chromium sulfate, manganese sulfate, iron sulfate, cobalt sulfate, nickel sulfate, ruthenium sulfate, rhodium sulfate, palladium sulfate, iridium sulfate and platinum sulfate.

Examples of the acetate are acetates of metals of Groups I-B, II-B, III-B, IV-B, V-B, VI-B and VIII of the Periodic Table, such as cupric acetate, chromium acetate, zinc acetate, cadmium acetate, cerium acetate, zirconium acetate, vanadium acetate, iron acetate, cobalt acetate, palladium acetate and nickel acetate.

Examples of the propionate are propionates of metals of Groups I-B, II-B, III-B, IV-B, V-B and VI-B of the Periodic Table, such as cupric propionate, chromium propionate, zinc propionate, cadmium propionate, cerium propionate, zirconium propionate and vanadium propionate.

As the transition metal oxide, there are suitably employed titanium dioxide, vanadium oxide, chromium oxide, manganese oxide, cupric oxide, zinc oxide, zirconium oxide, molybdenum oxide, silver oxide, cadmium oxide, cerium oxide, tungsten oxide, gold oxide, mercury oxide, thorium oxide, cupric oxide-copper chromate, cupric oxide-zinc oxide, chromium oxide-alumina, titanium dioxide-silica, titanium dioxide-zirconium oxide, and titanium dioxide-zinc oxide.

Examples of the metals of Group VIII of the Periodic Table are iron, cobalt, nickel, ruthenium, rhodium, palladium, iridium and platinum. These metals may be supported on a suitable carrier such as alumina.

As the halide of metals of Groups I-B, II-B, III-B, IV-B, V-B, VI-B and VIII of the Periodic Table, chlorides and bromides such as copper chloride, zinc chloride, cerium chloride, chromium chloride, titanium chloride, ferric chloride, cobalt chloride and nickel chloride are suitably employed in the present invention.

The following catalysts are preferably employed in the present invention.
(A) Solid acid: alumina, silica-alumina, nickel phosphate, cobalt aluminum phosphate, potassium hydrogensulfate, zinc sulfate, aluminum sulfate, cerium sulfate, titanium sulfate, ferric sulfate, tungstic acid
(B) Transition metal oxide: cupric oxide, molybdenum oxide, cupric oxide-zinc oxide, titanium dioxide-silica, titanium dioxide-zirconium oxide, titanium dioxide-zinc oxide
(C) Metals of Group VIII of the Periodic Table: rhodium, palladium, platinum, especially those supported on alumina
(D) Halide: ferric chloride, cobalt chloride, nickel chloride The starting material $\gamma$-vinyl-$\gamma$-butyrolactone is prepared by reacting butadiene with manganic acetate in the presence of acetic acid, acetic anhydride or potassium acetate and distilling the resulting reaction product. In the present invention, both the thus obtained $\gamma$-vinyl-$\gamma$-butyrolactone containing impurities such as acetic acid or acetic anhydride and the pure $\gamma$-vinyl-$\gamma$-butyrolactone obtained by purifying the reaction product may be suitably employed.

$\gamma$-Vinyl-$\gamma$-butyrolactone is contacted with a catalyst, if desired, with heating to cleave the $\gamma$-lactone to sorbic acid. The preparation procedures are very simple because sorbic acid can be prepared by merely contacting the $\gamma$-lactone with the catalyst, and also problems such as by-products, post-treatment and disposal of waste matters are reduced as compared with a conventional process. Further, the activity of the catalyst can be easily revived by a simple procedure such as washing. Thus, the process of the present invention is of great advantage in industrially preparing sorbic acid.

The reaction may be carried out in the vapor phase or in the liquid phase.

When preparing sorbic acid by contacting the $\gamma$-lactone with a catalyst in the vapor phase, the reaction is carried out by passing gaseous $\gamma$-vinyl-$\gamma$-butyrolactone through a reactor packed with a catalyst according to a conventional manner. For instance, a tubular reactor is packed with a catalyst. Since $\gamma$-vinyl-$\gamma$-butyrolactone is liquid at a normal temperature, a reactor equipped with a evaporator at the bottom of the reactor is employed and the $\gamma$-lactone is supplied to the evaporator and vaporized in the evaporator. The thus gasified $\gamma$-lactone is passed through the reactor. The concentration of the $\gamma$-lactone may be controlled by passing inert gas such as nitrogen or argon gas together with the gasified $\gamma$-lactone through the reactor.

During the reaction, the reaction temperature is maintained so that the $\gamma$-lactone can keep the gaseous state. Although the boiling point of $\gamma$-vinyl-$\gamma$-butyrolactone is about 225° C. at atmospheric pressure, when the reaction is carried out at a temperature of more than 300° C. for a long period of time, a catalyst tends to melt, or deteriorate, or scatter, or the produced sorbic acid tends to decompose or color. Therefore, it is preferable to reduce the pressure in the reaction system so as to drop the reaction temperature. Although the reaction temperature varies to some extent depending on the kind of the catalyst employed, the reaction is usually carried out at a temperature of 70° to 300° C., preferably at a temperature of 90° to 280° C. When the reaction temperature is lower than 70° C., it is difficult to produce sorbic acid by the reaction in the vapor phase. Also, the pressure in the reaction system is usually maintained at 1 to 300 mmHg to carry out the reaction at the above temperature range.

After the reaction is completed, the resulting gaseous reaction product is then cooled by a condenser such as an air condenser. By the cooling, the produced sorbic acid is deposited as white, needle-like crystals which are very pure, and a part of the unconverted $\gamma$-vinyl-$\gamma$-butyrolactone is liquefied. The unconverted $\gamma$-lactone may be reused. Since such an unconverted $\gamma$-lactone contains a relatively large amount of sorbic acid, the sorbic acid contained in the $\gamma$-lactone may be recovered by such a manner as precipitation and distillation before reusing the $\gamma$-lactone, by which the yield of sorbic acid is also increased.

When carrying out the vapor phase reaction on an industrial scale, a continuous reaction as stated below may also be carried out. The gaseous reaction product from a reaction tower is supplied to a middle stage of a continuous distillation tower, and then the gaseous unconverted $\gamma$-lactone is separated at a top of the tower and sorbic acid is taken out in a form of solid or liquid from a bottom of the tower. The separated $\gamma$-lactone is again supplied to the reaction tower.

In the present invention, there may be applicable any of conventional processes such as fixed bed process, fluidized bed process and moving bed process.

When preparing sorbic acid by contacting $\gamma$-vinyl-$\gamma$-butyrolactone with a catalyst in the liquid phase, the reaction may be carried out by a batchwise operation or a continuous operation. In a batchwise operation, the $\gamma$-lactone is merely admixed with a catalyst. In a continuous operation, the $\gamma$-lactone is passed through a reactor packed with a catalyst.

Although the reaction takes place even at a normal temperature, the reaction is usually carried out at an elevated temperature since the reaction rate is accelerated. In the present invention, the reaction temperature is maintained at 30° to 250° C., preferably at 70° to 170° C. The reaction is carried out for 10 minutes to 30 hours. After the completion of the reaction, the produced sorbic acid is recovered from the reaction liquid. In case of a batchwise operation, a catalyst is separated by filtration before recovering sorbic acid. From the reaction liquid, crystals of sorbic acid are precipitated by cooling, distillation or carrier distillation. In case of recovering sorbic acid by carrier distillation, a carrier such as petroleum distillate, dodecane or tetradecane is added to the reaction liquid, and then sorbic acid is distilled together with the carrier and is separated from the carrier as crystals by cooling the resulting distillate. Sorbic acid is obtained as white crystals.

In the present invention, if desired, to smoothly carry out the reaction the starting material $\gamma$-vinyl-$\gamma$-butyrolactone may be dissolved in an organic solvent having no effect on the reaction and such a solution may be subjected to the reaction in the vapor or liquid phase. Examples of the organic solvent are carboxylic acids such as acetic acid, glacial acetic acid, propionic acid and butyric acid, esters of the carboxylic acid such as ethyl acetate, ethyl propionate and methyl butyrate, ethers such as diphenyl ether, dioxane and ethylene glycol diethyl ether, hydrocarbons such as petroleum distillate having a boiling point at atmospheric pressure of 80° to 240° C., isooctane, dodecane, dodecene and tetradecane, halogenated hydrocarbons such as carbon tetrachloride, dichlorododecane and 1,5-dibromopentane, ketones such as methyl ethyl ketone, acetophenone, cyclohexanone and sym-dichloroacetone, alcohols such as 2-ethylhexanol and n-decanol, and esters such as diethyl glutarate and ethyl acetoacetate. Before recovering sorbic acid from the reaction mixture, these organic solvents may be distilled off. Also, when the recovery and purification of sorbic acid are made by means of carrier distillation, the organic solvent having a function as a carrier is advantageously selected. Further, when the same organic solvent as that used in reviving the activity of catalyst by washing is employed, adhesion of tarry materials to a catalyst is reduced and the procedure of reviving the activity becomes easy.

Tarry materials adhere to a catalyst during the use for a long period of time and make the activity of catalyst lower. When such catalysts of low activity are reused, they are washed with an organic solvent such as alcohols, acetone, ethers and carboxylic acid esters. The washing may be effected by agitating a mixture of a catalyst and an organic solvent, or pouring an organic solvent into a tube or cylinder packed with a catalyst. Such a washing procedure may be repeated. The total amount of the organic solvent used in washing is from 1 to 50 times the weight of the catalyst. Usually, the washing is repeated until the washing liquid becomes colorless and transparent.

The present invention is more specifically described and explained by means of the following Examples.

EXAMPLE 1

A glass tubular reactor having an inner diameter of 20 mm. and a length of 30 cm. which was equipped with a evaporator at a bottom thereof was charged with 10 g. of potassium hydrogensulfate as a catalyst. Further, 5 g. of γ-vinyl-γ-butyrolactone was supplied to the evaporator. The gas of the γ-lactone was passed through the reactor at a temperature of 130° to 135° C. under a reduced pressure of 5 to 7 mmHg. The resulting gas obtained from the top of the tubular reactor was collected in a trap for air cooling to give needle-like crystals of sorbic acid. The conversion of the γ-lactone was 32% and the selectivity for sorbic acid was 81%.

The melting point of the obtained crystals was 133° to 135° C. Also, as a result of measuring the infrared absorption spectrum, absorptions were observed at 1260, 1000, 1695, 1640, 1680 and 1705 cm.$^{-1}$ and the spectrum agreed with that of an authentic sorbic acid. Thus, it was confirmed that sorbic acid was prepared in high yield.

Controls 1 and 2

The procedures of Example 1 were repeated except that the use of a catalyst was omitted (Control 1) and also except that the use of a catalyst was omitted and the reaction temperature was maintained at 300° C. (Control 2).

In both cases, crystals of sorbic acid were not obtained. As a result of measuring the infrared absorption spectrum, it was confirmed that a trace of sorbic acid was merely formed.

EXAMPLES 2 to 20

In accordance with the procedures of Example 1, sorbic acid was prepared by employing the catalyst as shown in Table 1.

The results are shown in Table 1.

Table 1

| Example No. | Catalyst | Amount of catalyst (g.) | Reaction temperature (°C.) | Reaction pressure (mmHg) | Conversion (%) | Selectivity (%) |
| --- | --- | --- | --- | --- | --- | --- |
| 2 | Cobalt aluminum phosphate | 5.0 | 247 | 10 | 24 | 79 |
| 3 | Silica-alumina (85 : 15) | 20.0 | 163 | 5 | 18 | 83 |
| 4 | Cupric oxide-zinc oxide | 49.6 | 196 | 10 | 9 | 75 |
| 5 | Chromium oxide-alumina | 30.0 | 245 | 10 | 15 | 78 |
| 6 | Molybdenum oxide | 9.0 | 275 | 10 | 13 | 75 |
| 7 | Platinum-alumina (Supporting ratio of platinum: 1%) | 20.0 | 237 | 10 | 16 | 77 |
| 8 | Palladium acetate-alumina (Supporting ratio of palladium acetate: 5%) | 18.0 | 265 | 10 | 10 | 71 |
| 9 | Boric acid | 3.0 | 145 | 7 | 11 | 70 |
| 10 | Tungstic acid | 2.0 | 249 | 10 | 17 | 76 |
| 11 | Silicomolybdic acid (triacontahydrate) | 4.0 | 133 | 5 | 21 | 80 |
| 12 | Cobalt chloride | 2.0 | 207 | 10 | 9 | 75 |
| 13 | Nickel chloride | 2.0 | 221 | 10 | 15 | 78 |
| 14 | Aluminum sulfate | 2.0 | 170 | 10 | 27 | 82 |
| 15 | Rhodium-alumina (Supporting ratio of rhodium: 0.5%) | 10.0 | 240 | 9 | 10 | 68 |
| 16 | Alumina | 20.0 | 210 | 10 | 20 | 78 |
| 17 | Copper phosphate | 5.0 | 255 | 10 | 19 | 80 |
| 18 | Zinc phosphate | 10.0 | 245 | 10 | 17 | 77 |
| 19 | Cobalt calcium phosphate | 10.0 | 250 | 10 | 18 | 77 |
| 20 | Copper aluminum phosphate | 5.0 | 245 | 10 | 15 | 76 |

EXAMPLE 21

A one liter flask equipped with a stirrer was charged with 45.0 g. of γ-vinyl-γ-butyrolactone, 20.0 g. of ferric sulfate and 100 ml. of propionic acid. The reaction was carried out at a temperature of 141° C. for 2.5 hours with agitation. After the completion of the reaction, the catalyst was separated from the resulting reaction mixture by filtration. A part of the obtained mother liquor was taken out, and the yield of sorbic acid was calculated by acidifying the liquor with hydrochloric acid and measuring the absorbance at 263 mμ. The yield of sorbic acid to the consumed γ-lactone was 93.7%.

From the obtained mother liquor, 90 g. of propionic acid was distilled off at a temperature of 52° C. under a pressure of 20 mmHg, and then 500 ml. of a cold water was added to the mother liquor to precipitate the crystals. After separating the crystals by filtration, recrystallization was effected in a usual manner to give white crystals. The melting point of the thus obtained crystals was 133° to 135° C. Also, the infrared absorption spectrum of the crystals agreed with that of an authentic sorbic acid and it was confirmed that sorbic acid was obtained in high yield.

EXAMPLES 22 to 26

In accordance with the procedures of Example 21, sorbic acid was prepared by employing the catalyst as shown in Table 2.

The results are shown in Table 2.

Table 2

| Example No. | Catalyst | Reaction time (hour) | Yield of sorbic acid (%) |
|---|---|---|---|
| 22 | Aluminum sulfate | 7.5 | 93.3 |
| 23 | Cerium sulfate | 2.3 | 94.8 |
| 24 | Titanium sulfate (pentacosahydrate) | 5.0 | 89.7 |
| 25 | Potassium hydrogen-sulfate | 3.0 | 90.0 |
| 26 | Cupric sulfate (pentahydrate) | 5.5 | 90.1 |

EXAMPLE 27

The procedures of Example 21 were repeated except that the use of propionic acid was omitted and the reaction was carried out at a temperature of 150° C. for 20 minutes so that 20% by weight of γ-vinyl-γ-butyrolactone was converted. The selectivity was 93%.

EXAMPLE 28

The procedures of Example 21 were repeated except that acetic acid was employed instead of propionic acid and the reaction was carried out at a temperature of 120° C. for 5 hours. The yield of sorbic acid to the consumed γ-lactone was 90.2%.

EXAMPLE 29

A one liter flask equipped with a stirrer was charged with 90.2 g. of γ-vinyl-γ-butyrolactone, 37.0 g. of ferric sulfate hydrate and 500 ml. of a petroleum distillate (commercially available under the registered trademark "Isopar G" made by Esso Standard Petroleum Co., Ltd.) mainly consisting of hydrocarbon having 9 to 11 carbon atoms and having a boiling point at atmospheric pressure of 158° to 177° C. The reaction was carried out at a temperature of 180° C. for 45 minutes with agitation. The yield of sorbic acid to the consumed γ-lactone was 90.3%. After removing the catalyst from the resulting reaction mixture by filtration, the resulting mother liquor was subjected to a carrier distillation at 150° to 165° C. under 3 mmHg while supplying the petroleum distillate to give white crystals of sorbic acid.

EXAMPLE 30

A one liter flask equipped with a stirrer was charged with 11.2 g. of γ-vinyl-γ-butyrolactone, 2.7 g. of zinc chloride and 100 g. of propionic acid. The reaction was carried out at a temperature of 140° C. for 4 hours with agitation. The yield of sorbic acid to the consumed γ-lactone was 73.2%.

After removing the catalyst from the resulting reaction mixture, propionic acid was distilled off at 52° C. under 20 mmHg and then 100 ml. of cold water was added to the reaction mixture to precipitate the crystals of sorbic acid. The crystals were filtered and then washed with petroleum ether. The crystals were further dissolved in hot water and thereto active carbon was added. After filtering the active carbon, the crystals were recrystallized by cooling the filtrate. The melting point of the recrystallized sorbic acid was 133° to 134° C. Also, the infrared absorption and nuclear magnetic resonance spectrums of the crystals agreed with those of an authentic sorbic acid.

EXAMPLES 31 to 43

The procedures of Example 30 were repeated except that the catalyst shown in Table 3 was employed instead of zinc chloride.

The results are shown in Table 3.

Table 3

| Example No. | Catalyst | Yield of sorbic acid (%) |
|---|---|---|
| 31 | Chrominum acetate (monohydrate) | 57.1 |
| 32 | Cupric acetate | 64.4 |
| 33 | Cerium chloride (heptahydrate) | 60.9 |
| 34 | Chromium chloride (hexahydrate) | 68.3 |
| 35 | Titanium chloride | 55.0 |
| 36 | Cupric chloride | 73.3 |
| 37 | Zinc acetate | 63.8 |
| 38 | Vanadium acetate | 72.1 |
| 39 | Palladium acetate | 69.8 |
| 40 | Chromium propionate | 76.1 |
| 41 | Cupric propionate | 78.1 |
| 42 | Zinc propionate | 63.9 |
| 43 | Vanadium propionate | 69.9 |

EXAMPLE 44

The procedures of Example 30 were repeated except that the use of propionic acid was omitted and the reaction was carried out until 20% by weight of γ-vinyl-γ-butyrolactone was converted. The selectivity was 93%.

EXAMPLE 45

The procedures of Example 30 were repeated except that triethylene glycol diethyl ether was employed as a solvent instead of propionic acid. The yield of sorbic acid to the consumed γ-lactone was 83.5%.

EXAMPLE 46

A one liter flask equipped with a stirrer was charged with 30.0 g. of γ-vinyl-γ-butyrolactone, 14.3 g. of powders of silica-alumina (mixing ratio: 71:29) and 70 g. of propionic acid. The reaction was carried out at a temperature of 140° C. for 14 hours with agitation. After the completion of the reaction, the catalyst was separated from the resulting reaction mixture by filtration. A part of the obtained mother liquor was taken out, and the yield of sorbic acid was calculated by acidifying the liquor with hydrochloric acid and measuring the absorbance at 263 mμ. The yield of sorbic acid to the consumed γ-lactone was 84.0%. To the mother liquor was added water in an amount of two times the mother liquor and the cooling was effected to precipitate the crystals of sorbic acid.

The filtered catalyst was added to 30 ml. of acetone and was washed by agitating for 10 minutes. After filtering the catalyst, the catalyst was further washed with 30 ml. of acetone. The washing liquid was colorless and transparent. After washing, the catalyst was filtered and dried. Employing the washed catalyst, the preparation of sorbic acid was carried out in the same manner as above. Such procedures of reaction and washing were repeated five times. The yield of sorbic acid to the consumed γ-lactone in the fifth reaction was 79.8%.

As a control, the procedures of the above were repeated except that a strongly acidic styrene-type cation-exchange resin (commercially available under the registered trademark "Amberlyst XN-1004" made by Rohm & Haas Co.) was employed instead of the silica-alumina catalyst. The yield of sorbic acid in the fifth reaction was only 31.0%.

EXAMPLES 47 to 57

The procedures of Example 46 were repeated except that the catalyst shown in Table 4 was employed instead of the silica-alumina catalyst.

The results are shown in Table 4.

Table 4

| Example No. | Catalyst | Yield of sorbic acid in the fifth reaction (%) |
|---|---|---|
| 47 | Tungstic acid | 68.4 |
| 48 | Zinc sulfate | 71.0 |
| 49 | Nickel phosphate | 74.5 |
| 50 | Cupric oxide | 49.6 |
| 51 | Titanium dioxide-silica | 76.0 |
| 52 | Titanium dioxide-zirconium oxide | 82.2 |
| 53 | Titanium dioxide-zinc oxide | 80.1 |
| 54 | Cupric oxide-zinc oxide | 51.9 |
| 55 | Palladium-alumina | 77.8 |
| 56 | Rhodium-alumina | 70.0 |
| 57 | Ferric chloride | 83.6 |

EXAMPLE 58

The procedures of Example 46 were repeated except that the use of propionic acid was omitted. The yield of sorbic acid to the consumed γ-lactone was 74.1%.

EXAMPLE 59

The procedures of Example 46 were repeated except that acetic acid was employed instead of propionic acid and the reaction was carried out at a temperature of 120° C. for 20 hours. The yield of sorbic acid to the consumed γ-lactone was 78.0%.

What we claim is:

1. A process for preparing sorbic acid which comprises contacting γ-vinyl-γ-butyrolactone with at least one catalyst selected from the group consisting of (A) a solid acid selected from the group consisting of clay minerals, salts and double salts of phosphoric acid with metals, sulfates, boric acid, tungstic acid, phosphotungstic acid, silicotungstic acid, molybdic acid, phosphomolybdic acid, silicomolybdic acid, acetates of metals of Groups I-B, II-B, III-B, IV-B, V-B, VI-B and VIII of the Periodic Table, and propionates of metals of Groups I-B, II-B, III-B, IV-B, V-B and VI-B of the Periodic Table, (B) transition metal oxides, (C) metals of Group VIII of the Periodic Table and (D) halides of metals of Groups I-B, II-B, III-B, IV-B, V-B, VI-B and VIII of the Periodic Table, and recovering the resulting sorbic acid.

2. The process of claim 1, wherein said at least one catalyst is a solid acid selected from the group consisting of potassium dihydrogenphosphate, dipotassium hydrogenphosphate, barium hydrogenphosphate, calcium hydrogenphosphate, sodium dihydrogenphosphate, disodium hydrogenphosphate, copper phosphate, magnesium phosphate, zinc phosphate, aluminum phosphate, titanium phosphate, zirconium phosphate, chromium phosphate, iron phosphate, cobalt phosphate, nickel phosphate, ruthenium phosphate, rhodium phosphate, palladium phosphate, iridium phosphate and platinum phosphate.

3. The process of claim 1, wherein said at least one catalyst is a solid acid selected from the group consisting of ammonium sulfate, sodium sulfate, sodium hydrogensulfate, potassium sulfate, potassium hydrogensulfate, beryllium sulfate, magnesium sulfate, calcium sulfate, strontium sulfate, barium sulfate, zinc sulfate, cadmium sulfate, aluminum sulfate, cerium sulfate, titanium sulfate, chromium sulfate, manganese sulfate, iron sulfate, cobalt sulfate, nickel sulfate, ruthenium sulfate, rhodium sulfate, palladium sulfate, iridium sulfate and platinum sulfate.

4. The process of claim 1, wherein said at least one catalyst is a halide of a metal selected from the group consisting of ferric chloride, cobalt chloride and nickel chloride.

5. The process of claim 1, wherein the γ-vinyl-γ-butyrolactone is contacted with a catalyst in the vapor phase.

6. The process of claim 1, wherein the γ-vinyl-γ-butyrolactone is contacted with a catalyst in the vapor phase in the presence of an inert gas or a gas of an organic solvent having no effect on the reaction.

7. The process of claim 6, wherein said organic solvent is a member selected from the group consisting of acetic acid, glacial acetic acid, propionic acid, butyric acid, petroleum distillate having a boiling point at atmospheric pressure of 80° to 240° C., isooctane, dodecane, dodecene and tetradecane.

8. The process of claim 1, wherein the γ-vinyl-γ-butyrolactone is contacted with a catalyst in the liquid phase.

9. The process of claim 1, wherein the γ-vinyl-γ-butyrolactone is contacted with a catalyst in the liquid phase in the presence of an organic solvent having no effect on the reaction.

10. The process of claim 9, wherein said organic solvent is a member selected from the group consisting of acetic acid, glacial acetic acid, propionic acid, butyric acid, petroleum distillate having a boiling point at atmospheric pressure of 80° to 240° C., isooctane, dodecane, dodecene and tetradecane.

11. The process of claim 1 wherein at least one catalyst is a clay mineral selected from the group consisting of alumina, silica, zeolite, bentonite, bauxite, activated clay, diatomaceous earth, silica-alumina, silica-magnesia and alumina-boric anhydride.

12. A process for preparing sorbic acid which comprises contacting γ-vinyl-γ-butyrolactone with, as a catalyst, a transition metal oxide selected from the group consisting of cupric oxide, molybdenum oxide, cupric oxide-zinc oxide, titanium dioxide-silica, titanium dioxide-zirconium oxide and titanium dioxide-zinc oxide, and recovering the resulting sorbic acid.

13. A process for preparing sorbic acid which comprises contacting γ-vinyl-γ-butyrolactone with, as a catalyst, a metal of group VIII of the Periodic Table selected from the group consisting of rhodium, palladium and platinum, and recovering the resulting sorbic acid.

* * * * *